United States Patent
Perrut et al.

(10) Patent No.: US 6,709,595 B1
(45) Date of Patent: Mar. 23, 2004

(54) METHOD AND INSTALLATION FOR SETTING IN ADSORBED STATE ON A POROUS SUPPORT ACTIVE COMPOUNDS CONTAINED IN A PRODUCT

(75) Inventors: Michel Perrut, Nancy (FR); Wieslaw Majewski, Laxou (FR)

(73) Assignee: Separex (Societe Anonyme), Champigneulles (FR)

( * ) Notice: Subject to any disclaimer, the term of this patent is extended or adjusted under 35 U.S.C. 154(b) by 0 days.

(21) Appl. No.: 10/088,829
(22) PCT Filed: Sep. 27, 2000
(86) PCT No.: PCT/FR00/02668
§ 371 (c)(1),
(2), (4) Date: Mar. 22, 2002
(87) PCT Pub. No.: WO01/23064
PCT Pub. Date: Apr. 5, 2001

(30) Foreign Application Priority Data

Sep. 27, 1999 (FR) .............................. 99 12005

(51) Int. Cl.[7] .............................................. B01D 11/00
(52) U.S. Cl. ........................ 210/634; 210/180; 210/182; 210/511; 210/669; 210/774; 422/256; 424/734; 426/425; 426/429
(58) Field of Search ................... 424/195.15, 195.16, 424/195.17, 195.18, 734; 426/425, 429; 210/634, 638, 639, 644, 645, 663, 669, 689, 770, 773, 774, 806, 177, 180, 182, 259, 266, 511; 422/256, 260

(56) References Cited

U.S. PATENT DOCUMENTS

| | | | | |
|---|---|---|---|---|
| 4,349,415 A | * | 9/1982 | DeFilippi et al. | 210/634 |
| 4,460,476 A | * | 7/1984 | McCaffrey et al. | 210/689 |
| 4,877,530 A | * | 10/1989 | Moses | 210/511 |
| 5,151,188 A | * | 9/1992 | Hopper et al. | 210/634 |
| 5,160,044 A | * | 11/1992 | Tan | 210/634 |
| 6,013,304 A | * | 1/2000 | Todd | 426/638 |
| 6,123,945 A | * | 9/2000 | Nakatsu et al. | 424/745 |

FOREIGN PATENT DOCUMENTS

| | | |
|---|---|---|
| EP | 0 379 963 A | 8/1990 |
| WO | WO 91/14373 A1 | 10/1991 |

OTHER PUBLICATIONS

Patent Abstracts of Japan; vol. 14, No. 382, (Aug. 17, 1990).

* cited by examiner

*Primary Examiner*—Joseph Drodge
(74) *Attorney, Agent, or Firm*—Dechert LLP

(57) ABSTRACT

The invention concerns a method and an installation for setting in adsorbed state, on a porous support, compounds contained in a product comprising a first step which consists in extracting the compounds by contacting the product with at least a solvent at supercritical pressure to obtain a mixture of extracts and solvent. The method is characterized in that it comprises a second step which consists in eliminating the water contained in the mixture of extracts and solvent, adjusting the temperature and pressure conditions so as to obtain, a first phase consisting of solvent in gaseous state and a second phase consisting of a mixture of liquids formed of solvent and extracts of the products; causing said two phases to trickle through a porous support adapted to adsorb the extracts; vaporizing the solvent contained in the second phase.

19 Claims, 1 Drawing Sheet

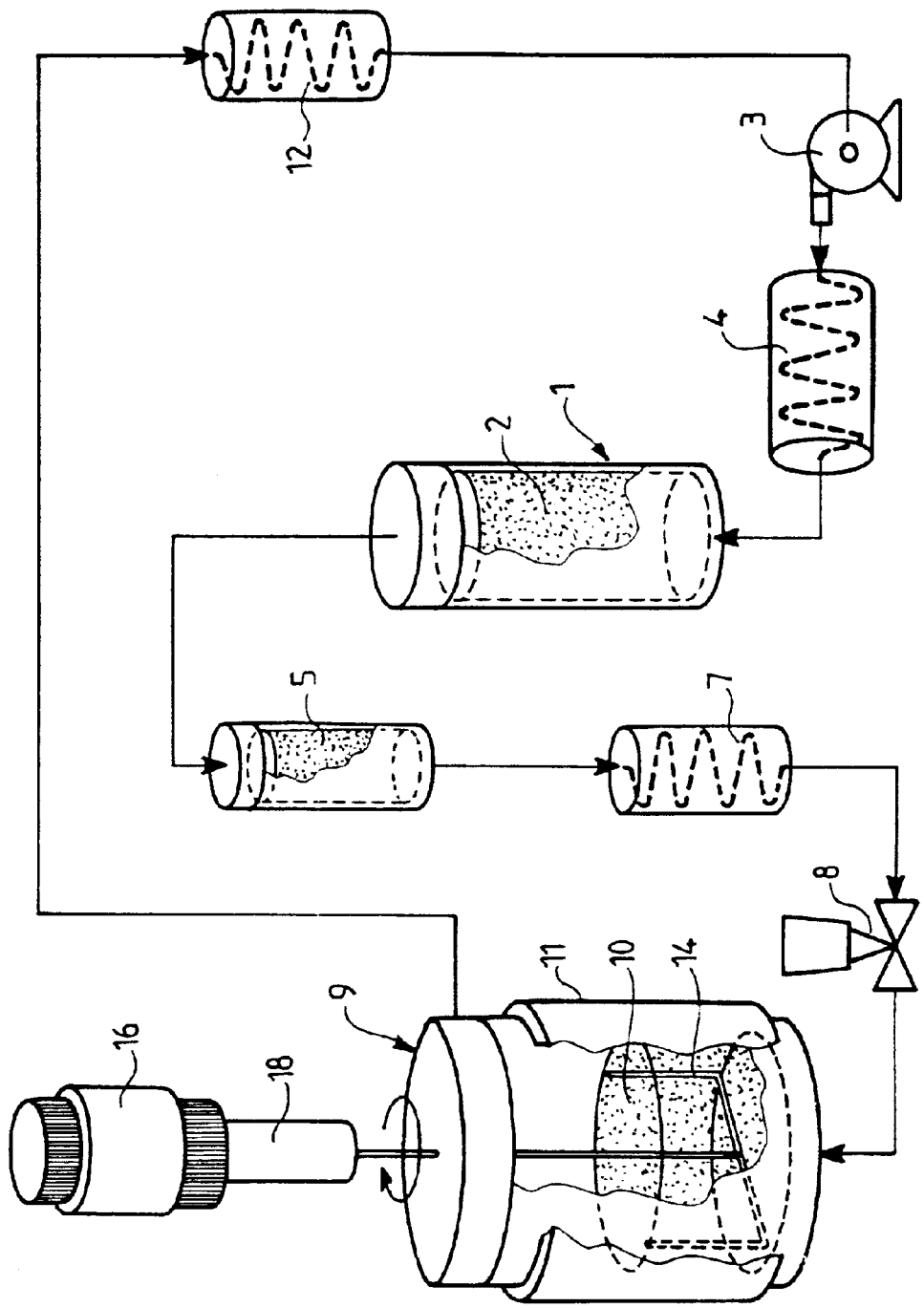
FIGURE UNIQUE

METHOD AND INSTALLATION FOR SETTING IN ADSORBED STATE ON A POROUS SUPPORT ACTIVE COMPOUNDS CONTAINED IN A PRODUCT

This application is a 371 of PCT/FR00/02668, filed Sep. 27, 2000, based on foreign application FRANCE 9912005, filed Sep. 27, 1999.

BACKGROUND OF THE INVENTION

The present invention relates to a method and an installation allowing, industrially, the setting in adsorbed state, on a porous support, of certain active compounds contained in natural or synthetic products. More precisely, such an operation will be effected after a preliminary phase during which said active compounds will be extracted from these products with the aid of a solvent taken to supercritical pressure, i.e. a fluid in supercritical state or a subcritical liquid.

In effect, it is known that bodies are generally known in three states, namely solid, liquid or gaseous, and that one passes from one to the other by varying the temperature and/or the pressure. Now, there is a point beyond which one can pass from the liquid state to the gaseous or vapour state without passing via a boiling or, inversely, a condensation, but continuously: this point is called the critical point.

It is also known that a fluid in supercritical state, i.e. a fluid which is in a state characterized either by a pressure and a temperature respectively greater than the critical pressure and temperature in the case of a pure body, or by a representative point (pressure, temperature) located beyond the envelope of the critical points shown in a diagram (pressure, temperature) in the case of a comparison with that observed in this same fluid in the state of compressed gas. The same applies to the so-called "subcritical" liquids, i.e. liquids which are in a state characterized either by a pressure higher than the critical pressure and by a temperature lower than the critical temperature in the case of a pure body, or by a pressure higher than the critical pressures and a temperature lower than the critical temperatures of the components in the case of a mixture (cf. on this subject the article by Michel PERRUT—Les Techniques de l'Ingénieur "Extraction by supercritical fluid, J 2 770-1 to Dec. 1999").

The considerable and modulatable variations of the solvent power of the supercritical fluids are, moreover, used in numerous methods of extraction (solid/fluid), fractionation (liquid/fluid), analytical or preparative chromatography, treatment of materials (ceramics, polymers . . . ). Chemical or biochemical reactions are also made in such solvents. It should be noted that the physico-chemical properties of carbon dioxide as well as its critical parameters (critical pressure: 7.4 MPa and critical temperature: 31° C.) make of it the preferred solvent in numerous applications, all the more so as it does not present any toxicity and is available at very low price in very large quantities. Non-polar solvent, the carbon dioxide taken to supercritical pressure sometimes has a co-solvent added thereto, constituted in particular by a polar organic solvent whose function is to considerably modify the solvent power, especially with respect to molecules presenting a certain polarity, ethanol often being used to that purpose. However, certain compounds are more favourably extracted with a light hydrocarbon having from 2 to 5 carbon atoms, and more favourably, from 2 to 4 carbon atoms, at supercritical pressure.

One of the principal advantages of the methods using fluids at supercritical pressure as solvents resides in the facility of effecting the separation between the solvent and the extracts and solutes, as has been described in numerous publications and, for certain important aspects of implementation, in French Patent FR-A-2 584 618. The interesting properties of these fluids have, moreover, been used for a long time in solid-fluid extraction and liquid-fluid fractionation, as has been described in the article mentioned above.

In the event of the extracts or solutes comprising very volatile products, such as odorant products, the mere separation by partial decompression bringing about separation of the solutes and their collection by phase separation with the fluid, is not very efficient and the fluid, even partially decompressed, still contains substantial quantities of such substances. In order to separate these substances from the fluid before its recycling, it is known to use an adsorbent bed which will fix these substances and purify the fluid, as described for example in Japanese Patent JP-A-02139003.

Finally, it is known that the extraction of natural products by a fluid at supercritical pressure leads to extracts of very high quality which are increasingly used in numerous applications. However, such extracts, lie, moreover, the extracts obtained with other means such as for example extraction by organic solvent, are often in the form of very viscous or even pasty products which are not easy to handle, with the result that their incorporation in solid supports, the dosage and the mixture with a matrix and possibly other active principles, within a solid excipient, are very difficult. One is sometimes obliged to place them in solution in an organic solvent in order to effect impregnation of a solid excipient, which is regrettable since there thus disappears a determining advantage in numerous applications for which any contact of the product with an organic solvent is to be avoided.

SUMMARY OF THE INVENTION

The present invention has for its object to propose means making it possible, for purposes of industrial production, to extract active principles, particularly of pharmaceutical, cosmetological, dietetic interest, from diverse raw materials in which they are diluted, in variable concentration, depending on the origin of these raw materials and the period of their harvesting, as is always the case for products of natural origin, and to fix the extract obtained in the course of extraction in an adequate porous matrix by impregnation in one and the same operation.

According to the invention, the operation of extraction by fluid at supercritical pressure is coupled with a second operation during which the separation of the extract mixed with the solvent fluid and the impregnation of a porous medium by this extract are effected simultaneously.

The present invention thus has for its object a method for setting in adsorbed state, on a porous support, compounds contained in a product, in which, during a first step, the extraction of the compounds is effected by contacting the product with at least one solvent fluid at supercritical pressure leading to the obtaining of a mixture of extracts and of solvent fluid, characterized in that, in a second step, the water contained in the mixture of extracts and of solvent fluid is eliminated, the temperature and pressure conditions are adjusted so as to obtain, in an enclosure, two phases, namely a first phase essentially constituted by the solvent fluid in the gaseous state and a second phase constituted by a mixture of liquids formed by solvent fluid and extracts of the product, these two phases are made to trickle through a porous support adapted to adsorb the extracts, the solvent fluid contained in the second phase is vaporized.

The elimination of the water will preferably be ensured by causing the mixture of extracts and of solvent fluid to trickle over a bed of adsorbent product adapted to fix the water selectively.

The solvent fluid may be constituted by pure carbon dioxide, nitrogen protoxide or a light hydrocarbon counting from 2 to 4 carbon atoms. The solvent fluid may be pure or possibly have one of more co-solvents added thereto. For example, the solvent fluid may in particular be constituted by a mixture of carbon dioxide with at least one co-solvent constituted by an alcohol and preferably ethanol, by a ketone and preferably acetone, by an ester and preferably ethyl acetate.

The first step of extraction may preferably be effected at a pressure included between 7.4 MPa and 80 Mpa, and preferably between 10 MPa and 40 MPa, and at a temperature included between 0° C. and 80° C. Similarly, the trickling of the two phases through the porous support may be effected at a pressure included between 1 MPa and 10 MPa, and preferably between 4 MPa and 8 Mpa, and at a temperature included between 0° C. and 80° C.

The present invention also has for its object an installation for extraction/impregnation of the type comprising an extractor containing a product from which it is desired to extract the compounds, which is traversed to that end by at least one solvent fluid at supercritical pressure, characterized in that it successively comprises, downstream of the extractor, means for eliminating the water contained in the extracted compounds, means adapted to create, in an impregnation enclosure containing a porous medium, two phases, namely a first phase essentially constituted by the solvent fluid in the gaseous state and a second phase constituted by a mixture of liquids formed by solvent fluid and the extracts of the product, so as to effect the adsorption by the porous medium of the extracted compounds. The impregnation enclosure may comprise means for contributing enthalpy, particularly constituted by a double envelope with circulation of heat-exchange fluid.

The installation may also comprise, downstream of the impregnation enclosure, means for condensation of the solvent fluid.

In a variant embodiment of the invention, the extractor may be constituted by a fractionating column operating in counter-flow, adapted for the treatment of liquid raw materials.

Various forms of embodiment of the present invention will be described hereinafter by way of non-limiting examples, with reference to the accompanying single Figure which schematically shows an installation for carrying out the method according to the invention.

As has been described in detail in the article and the Patent mentioned hereinabove, it is known that the methods of extraction and of fractionation using a fluid at supercritical pressure comprise two successive steps: a first step during which the solvent fluid is contacted with the raw material to be treated, under such pressure and temperature conditions that its solvent power with respect to the compounds to be extracted is high, and a second step during which the fluid is placed under such pressure and temperature conditions that its solvent power is very weak with respect to the products which it has extracted from the raw material during the earlier step, which allows the separation of these extracts, the fluid then being recycled. Unlike the conventional embodiments consisting in separating the two phases obtained during this second step in gravity or inertia separators, the method according to the invention consists in causing the mixture of these two phases to trickle within a porous medium.

It has been noticed that, if the operation is carried out without particular precaution, the extracts are not distributed homogeneously on and within the porous medium and, even by proceeding with stirring of this porous medium if it is in pulverulent or granular form, for example with the aid of a rotating turbine, lumps of variable size are generally obtained, resulting from the agglomeration of the particles of the porous medium by the extracts which, instead of penetrating in the pores, remain on the surface without homogeneous distribution. Moreover, natural products, capable of being advantageously treated by a method of this type, always having a certain content of water, the extracts always contain water of which the presence complicates their adsorption on the porous supports or excipients, as the majority of them have a great affinity for water, so that their structure and their mechanical properties are seriously altered by the water thus contributed by the fluid at the same time as the extracts envisaged.

On the contrary, when the water is trapped, particularly by a selective adsorbent, and the impregnation of the porous medium is then effected under determined pressure and temperature conditions, it is observed that, surprizingly, the extracts impregnate this porous medium in very homogeneous and reproducible manner, leading for example to a non-sticky powder presenting a good fluidity in the case of the initial porous medium also presenting these characteristics.

BRIEF DESCRIPTION OF THE INVENTION

An example of installation for carrying out the method according to the invention will be described hereinafter with reference to the single FIGURE showing components of a system for extraction.

DETAILED DESCRIPTION OF THE INVENTION

This installation is derived from a conventional unit of extraction by fluid at supercritical pressure intended for the discontinuous treatment of solid materials. It comprises an extractor 1 containing a basket 2 intended to receive the raw material to be treated, and a diaphragm pump 3 which distributes liquid carbon dioxide at the working pressure, through a heat exchanger 4 making it possible to heat the fluid to the working temperature. Unlike the conventional installations for extraction by fluid at supercritical pressure, the fluid emerging from the extractor 1 is conducted in a recipient 5 which contains a porous medium for selectively adsorbing water, such as in particular the molecular sieve 3A. The fluid which is under the same pressure and temperature conditions as those prevailing in the extractor 1, trickles through the porous medium where it abandons the water that it contains.

The recipient 5 is connected to a pressure reducing valve 8 via a heater-exchanger 7. The outlet of the valve 8 is connected to the bottom of an impregnation enclosure 9 which contains the porous medium 10 in which it is desired to adsorb the extracts. The enclosure 9 comprises heating means constituted for example by a double envelope 11 in which a heat exchange fluid circulates. The fluid leaving the recipient 5 is thus taken to a state of desired pressure and temperature determined during its passage in the exchanger 7 and the pressure reducing valve 8, so that it comprises a gaseous phase and a liquid phase. The heating means constituted by the double envelope 11 make it possible to vaporize liquid phase arriving in the impregnation enclosure 9, so as to maintain constant the level of liquid phase therein. Under these conditions, a gaseous phase is therefore had permanently in the impregnation enclosure 9, constituted by solvent fluid and a liquid phase constituted by the extracts and the solvent fluid.

The porous medium 10 is chosen as a function of the subsequent use which it is desired to make of the final product, whether it be a granular or pulverulent medium particularly adapted for use in dietetics, pharmacy or cosmetics, or a solid medium. In the most frequent case where this medium is in granular or pulverulent form, a particularly advantageous embodiment consists in string this porous medium within the impregnation enclosure 9 by any adequate means, for example by means of a turbine 14 moved by an electric motor 16 via a magnetic drive system 18.

The upper part of the enclosure 9 is joined to the pump 3 through a condenser 12.

Of course, it is possible, according to the invention, to use any other separation system, and the extractor 1 might be replaced by a fractionating column making possible the continuous or discontinuous treatment of raw materials in the liquid state, the fluid emerging from the column being treated in the same manner as that described previously.

In a variant of the invention, an auxiliary pump is used for introducing in the extractor 1 one or more organic co-solvents making it possible to modify the solvent power and the polarity of the solvent fluid. It is often chosen to add ethanol which may be of alimentary quality or CODEX depending on the destination of the products thus elaborated. A light hydrocarbon having between 2 and 8 carbon atoms may also favourably be used as co-solvent. In the case of a co-solvent being used, a porous medium which is not altered by this co-solvent will naturally be chosen. Moreover, at the end of the extraction-impregnation operation, care will be taken to scavenge the porous medium with pure solvent fluid without co-solvent in order to eliminate the adsorbed co-solvent.

It has been ascertained that, under these conditions, an excellent diffusion of the fluid was obtained through the pores of the porous medium, and, correlatively, the entrainment in these latter of the extracts and their adsorption in the pores.

A contribution of enthalpy is required to maintain a constant quantity of fluid in the liquid state within the impregnation enclosure 9, in proportion as the fluid coming from extraction is injected and as an identical delivery of fluid which emerges from this enclosure in the gaseous state is therefore vaporized. This contribution of enthalpy must be carefully adjusted in order to avoid, if it is insufficient, either the accumulation of liquefied fluid in the impregnation recipient which would finish by emerging in this liquid form, taking along part of the extracts, or, if it is too great, the total vaporization of the fluid and the non-controlled precipitation of the extracts.

As will be illustrated in the following examples of implementation of the method and of the installation according to the invention, it is surprizing to effect extraction and to obtain a very homogeneous impregnation of different excipients by the extracts in one operation, without ever having to manipulate the extracts themselves, which can but avoid all risk of degradation by oxidation in air or by exposure to heat, since any contact with air is avoided and all the operations are conducted at a temperature close to ambient temperature.

Several examples of the invention which were carried out with the installation described hereinabove and whose operational parameters were as follows, will be described hereinafter:

| | |
|---|---|
| Volume of the basket 2 | 0.5 l |
| Flowrate of the pump 3 | 1 to 5 kg/hr |
| Working pressure | of the order of 30 MPa |
| Working temperature | between 10° C. and 80° C. |
| Contents of recipient 5 | 100 g of zeolite 3A |
| Volume of impregnation enclosure 9 | 4.5 l |
| Porous material | Maltodextrine powder of alimentary quality obtained by partial hydrolysis of maize amide |
| Speed of rotation of the turbine 18 | 120 revs/minute |

EXAMPLE 1

Extraction and Impregnation of KAVA-KAVA

Kava-kava is the local name of a wild shrub of the Pacific islands, identified as Piper methysticum or Piper wichmannu, whose roots contain products of great pharmacological interest called kavalactones, widely used in different forms as natural tranquillizer and euphoriant.

The extraction was conducted on 100 g of powder of dried roots, ground towards about 200 $\mu$m, with a flowrate of 3 kg/hr of carbon dioxide at 25 MPa and 40° C., and furnished an extract which is in the form of a very viscous, dark yellow paste with characteristic odour. After adsorption of the water, the pressure of the fluid was reduced to 6 MPa and injected via the bottom into the impregnation enclosure 9 containing 100 g of maltodextrine. It was observed that the compressed gas leaving the top of the enclosure 9 presented a constant temperature close to 40° C. in established operation. After having continued the operation for 510 mins., the impregnation enclosure 9 was decompressed and 114.8 g of a bright yellow powder was recovered therein, which presented the characteristic odour of the extract of kava-kava and flowing without problem in the absence of any lump or agglomerate, ideal for manufacturing tablets, possibly mixed with an excipient or other active principles. A sample of this powder was re-extracted with chloroform and analyzed by gas-chromatography. It was ascertained that the extract fixed on the maltodextrine was constituted by 89% by mass of kavalactones whose identification makes it possible to verify that the relative abundance of each of these compounds is conforming to what is found in a conventional extract. This therefore confirms both the high selectivity of the extraction by the carbon dioxide at supercritical pressure and the complete fixation of the extract on the maltodextrine.

EXAMPLE 2

Extraction and Impregnation of KAVA-KAVA

A second operation was proceeded with under conditions identical to those used in Example 1, except that, this time, the initial mass of maltodextrine was only 50 g. After 510 mins. of operation, 65.6 g of powder were obtained, whose characteristics are identical to those of the powder obtained in Example 1, except that its colour and odour are more intense. An analysis of the fixed extract revealed a percentage of kavalactones of 91% by mass, with a distribution between the different compounds virtually identical to that observed in the preceding Example. This shows that the maltodextrine may be charged with at least 30% by mass of extract.

EXAMPLE 3

Extraction and Impregnation of KAVA-KAVA

A third operation was proceeded with under conditions identical to those used in Example 2, except that, this time, a porous medium was chosen, composed of an intimate mixture of powders of maltodextrine and soja lecithin of alimentary quality, at a rate of 45 g of maltodextrine for 5 g of lecithin. The initial mass of porous medium was fixed at 50 g. After 510 mins. of operation, 64.2 g of powder were obtained, whose characteristics proved to be close to those of the powder obtained in Example 1, except that its colour and odour are more intense. An analysis of the fixed extract led to a percentage of kavalactones of 90% by mass, with a distribution between the different compounds virtually identical to that observed in the preceding Example. This powder thus presents the advantage, with respect to the powders obtained in Examples 1 and 2, of being more easily dispersed in water, giving rise to a turbidity resembling that obtained by diluting pastis in water. It may therefore be used not only in dry formulations, such as tablets, but also in the form of a powder to be mixed in water in order to prepare a drinkable potion.

EXAMPLE 4

Extraction and Impregnation of a Spice (Curcuma)

The extraction was conducted on a total mass of 800 g of ground Curcuma, distributed in 4 batches of 200 g placed successively in the extractor 1 with a flowrate of 2.4 kg/hr of carbon dioxide at 40° C. and 29 MPa. After elimination of the water, the pressure of the latter was reduced to 5 MPa and it was injected via the bottom in the impregnation enclosure 9 containing a mass of 400 g of maltodextrine which was successivly impregnated with the extracts issuing from the four batches. After having continued the operation for four periods of 50 mins. each, 445 g of a very homogeneous orange powder were recovered, presenting the odour and characteristic taste of the extract of Curcuma.

EXAMPLE 5

Extraction and Impregnation of a Mixture of Spices (Black Pepper+Mild Paprika)

One proceeded with an operation of extraction and impregnation of the spices under conditions identical to those used in Example 4, except that, this time, the charge was constituted by a mixture of 180 g of pepper and 20 g of paprika. After having passed 8.4 kg of carbon dioxide, 412 g of very homogeneous red powder were obtained, in the absence of lump or agglomerate.

What is claimed is:

1. Method for setting in absorbed state, within on a porous support, compounds contained in a starting material, comprising
   a. contacting, at supercritical pressure, the starting material with a solvent fluid comprising at least one solvent to obtain a mixture of extracts and solvent fluid;
   b. contacting the mixture of extracts and of solvent fluid with a bed of absorbent product adapted to absorb water selectively;
   c. adjusting the temperature and pressure conditions of the mixture of extracts and solvent fluid exiting from the absorbent bed to obtain a first phase consisting essentially of the solvent fluid in the gaseous state and a second phase comprising a mixture of solvent fluid and extracts from the starting material;
   d. contacting the first and second phases with a porous support adapted to absorb the extracts;
   e. vaporizing the solvent fluid contained in the second phase.

2. Method according to claim 1, wherein the solvent fluid is constituted by carbon dioxide, by nitrogen protoxide or by a light hydrocarbon having from 2 to 8 carbon atoms.

3. Method according to claim 2, wherein the solvent fluid has at least one co-solvent added thereto.

4. Method according to claim 3, wherein the solvent fluid co-solvent is constituted by an alcohol, and/or by a ketone, and/or by an ester.

5. Method according to claim 1, wherein the solvent fluid is a pure fluid.

6. Method according to claim 1, wherein the solvent fluid has at least one co-solvent added thereto.

7. Method according to claim 6, wherein the co-solvent is constituted by an alcohol, and/or by a ketone, and/or by an ester.

8. Method according to one of claims 1–7, wherein step (a) is effected at a pressure included between 7.4 MPa and 80 MPa, and at a temperature included between 0° C. and 80° C.

9. Method according to claim 8, wherein step (d) is effected at a pressure included between 1 MPa and 10 MPa, and at a temperature included between 0° C. and 80° C.

10. Method according to claim 8, wherein step (a) is effected at a pressure included between 10 MPa and 40 MPa.

11. Method according to claim 10, wherein step (d) is effected at a pressure included between 1 MPa and 10 MPa, and at a temperature included between 0° C. and 80° C.

12. Method according to one of claims 1–7, wherein step (d) is effected at a pressure included between 1 MPa and 10 MPa, and at a temperature included between 0° C. and 80° C.

13. Method according to claim 12, wherein step (a) is effected at a pressure included between 4 MPa and 8 MPa.

14. Installation for extraction/impregnation of the type comprising, in serial connection:
   an extractor adapted to accept a starting material for extraction and to allow at least one solvent fluid at supercritical pressure pass over the starting material producing a mixture of solvent fluid and extracted compounds;
   an vessel comprising a material selected to absorb water from the mixture of solvent fluid and extracted compounds;
   an impregnation enclosure comprising a porous medium selected to absorb extracts, the enclosure associated with means for contributing enthalpy, the means adapted to create, in the impregnation enclosure, a first phase consisting essentially of the solvent fluid in the gaseous state and a second phase comprising a mixture of liquids formed by solvent fluid and the extracts of the product, the porous medium and enthalpy effective to effect absorption by the porous medium of extracted compounds.

15. Installation according to claim 14, wherein the means for contributing enthalpy is a double envelope jacket for circulating heat-exchange fluid.

16. Installation according to claim 14, comprising a pressure reducing valve between the vessel and the impregnation enclosure.

17. Installation according to one of claims 14–16, wherein the extractor is a fractionating column operating in counter-flow, adapted for the treatment of liquid raw materials.

18. Installation according to claim 17, comprising an injector of injecting an organic co-solvent within the solvent fluid.

19. Installation according to one of claims 14–16, comprising an injector for injecting an organic co-solvent within the solvent fluid.

* * * * *